United States Patent [19]

Braid, deceased

[11] Patent Number: 4,530,770
[45] Date of Patent: Jul. 23, 1985

[54] PHENOL-HINDERED PHENOL BORATES AND LUBRICANT COMPOSITIONS CONTAINING SAME

[75] Inventor: Milton Braid, deceased, late of Haddonfield, N.J., by Gerassimos Frangatos, executor

[73] Assignee: Mobil Oil Corporation, New York, N.Y.

[21] Appl. No.: 523,524

[22] Filed: Aug. 16, 1983

[51] Int. Cl.³ .............................................. C10M 1/54
[52] U.S. Cl. .............................. 252/49.6; 260/462 R; 260/462 C; 252/400.41; 252/400 R
[58] Field of Search .......................... 252/49.6, 400.41; 260/462 R, 462 C

[56] References Cited

U.S. PATENT DOCUMENTS 3,356,707 12/1967 Hinkamp et al. .................. 252/49.6
4,392,973 7/1983 Moore et al. ...................... 252/49.6

Primary Examiner—Jacqueline V. Howard
Attorney, Agent, or Firm—Alexander J. McKillop; Michael G. Gilman; Claude E. Setliff

[57] ABSTRACT

The invention provides phenol-hindered phenol borates as lubricant and fuel additives. They provide exceptional antioxidant properties in these media.

25 Claims, No Drawings

PHENOL-HINDERED PHENOL BORATES AND LUBRICANT COMPOSITIONS CONTAINING SAME

BACKGROUND OF THE INVENTION

1. Field of the Invention

The invention relates to lubricant and fuel antioxidants. More particularly, it relates to lubricants and fuels to which have been added certain phenol esters of hindered phenyl borates.

2. Discussion of the Prior Art

Various compounds have been developed to combat lubricant and fuel oxidative deterioration. The primary object, of course, was to provide active antioxidants. The next most important object was to discover active boron-containing esters that would also be stable under use conditions. Among the many compounds that have been provided by the art are certain boron esters. U.S. Pat. No. 3,356,707, for example, teaches a class of borate esters, where at least one of the ester groups is a 2,6-dialkylphenol group. The other two ester groups can be additional phenolic residues or simple alkyl, aryl or glycol residues derived from hydroxyl-combining hydrocarbons. The borate esters thus produced are taught to be highly stable under hydrolytic conditions and to have a high degree of antioxidant activity. These are said to overcome the general tendancy of boron esters to hydrolyze and to be destroyed, thus making them unattractive for use in liquid hydrocarbons.

We have found a class of boron esters of hindered phenyl borates, which are only partially hydrolytically stable, and function with a very high degree of antioxidant activity by virtue of that partial but selective hydrolytic instability.

SUMMARY OF THE INVENTION

In accordance with the invention there are provided lubricant and liquid fuel compositions comprising a lubricant or fuel and an antioxidant amount of a compound of the formula

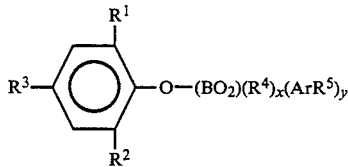

wherein $R^1$ and $R^2$ are tertiary alkyl or aralkyl groups containing 4 to 18 carbon atoms in any isomeric arrangement in which the carbon atoms bonded to the phenyl ring is itself bonded to three other carbon atoms, $R^3$ is hydrogen, a hydrocarbyl group preferably alkyl or aralkyl, containing 1 to 18 carbon atoms, also in any isomeric arrangement an alkoxy group containing 1 to 16 carbon atoms, a carbalkoxy group containing 2 to 12 carbon atoms, a alkylaminomethylene group containing 4 to 16 carton atoms or an alkylcarboxylmethylene group containing 3 to 16 carbon atoms, $R^4$ is hydrogen, a

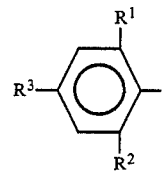

group or a $C_1$ to $C_6$ alkyl group, Ar is a $C_6$ to $C_{12}$ aromatic group, $R^5$ may be the same as $R^3$, a hydroxyarylthio group or a hydroxyarylamino group, x may be from 0 to 2, y may be 1 or 2.

It will be understood that, while some of the products are made with amounts of reactants that are not stoichiometric in terms of molar ratio, a substantial amount thereof will comprise a compound of the stated formula.

DISCUSSION OF SPECIFIC EMBODIMENTS

There are a number of known ways to make the compounds used in the compositions of this invention. One way is to react boric acid with sufficient 2,6-ditertiary-alkyl phenol to displace one of the acid hydroxyls, followed by reacting the remaining hydroxyls with unhindered phenol. In this reaction, the order of reaction, of course, can be reversed. That is, the unhindered phenol can be reacted first. Reaction temperatures used are sufficiently high to remove the water produced in the esterification reaction, i.e., it is at least 100° C. and preferably about 110° C. to about 130° C. at atmospheric pressure and correspondingly lower at reduced pressure. Alternatively, a solvent such as benzene, toluene or xylene may be used to remove water by azeotropic distillation at the appropriate temperature for the particular binary azeotropic system.

A second method involves transesterification of the triester borates. For example, tributyl borate can be heated at from about 115° C. to 275° C. with hindered phenol and then with unhindered phenol so the product contains at least one of each of the two types of phenols. Further, in a third method a product containing a substantial, or predominant, amount of the product of the above formula can be made by reacting boric oxide ($B_2O_3$) or equivalent compound with a mixture of hindered and unhindered phenols at from about 110° C. to about 250° C. Effective triester borates can be made by reacting these in respective molar ratios of from 1:2:1 to 1:4:4 but the ratio of molar of hindered phenol to atoms of boron must be at least 1:1. It is an important aspect of this invention that, while other phenyl and/or alkyl boron ester groups may transesterify or interchange if not removed from the reaction mixture, the boron esters of hindered phenols once formed undergo no or negligible degrees of transesterification, or other replacement.

Among the useful unhindered phenols that may be mentioned are
- n-butylcatechol, di-sec-butylcatechol, n-hexylrosorcinol,
- 2,4-di-iso-butylphenol, t-butyl-p-cresol, amylhydroquinine,
- di-amylhydroquinone, dihexylnaphthol, 2,2'-thiobis-(4-t-amyl)phenol,
- 2,2'-thiobis-(4-t-octyl)phenol, carbobutoxylphenol, 4-anilinophenol and the like.

The hindered phenols that are contemplated have the formula

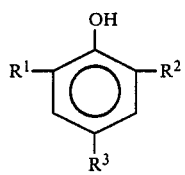

where $R^1$, $R^2$ and $R^3$ are as defined hereinabove. In connection with the definition of these three groups, the hydrocarbyl group, as mentioned in the Summary may be an alkyl, alkenyl, cycloalkyl, aryl, aralkyl or alkaryl group which may have substituted thereon other groups, e.g., an aralkoxy group, an alkylthio group or the like. The useful hindered phenols include 2,6-di-t-butylphenol, 2,6-di-t-butyl-4-butoxyphenol, 2,6-di-t-butyl-4-carbobutoxyphenol and 3,6-di-t-butyl-4-hydroxybenzyl pivalate and the like.

Of particular significance, in accordance with the present invention, is the ability to improve certain properties of fuels as well as the friction and oxidation properties of oleaginous materials such as lubricating media which may comprise either a mineral oil or a synthetic oil or mixtures thereof or a grease therefrom. In general, mineral oils, both paraffinic and naphthenic oils and mixtures thereof, employed as the lubricating oil or grease vehicle, may be of any suitable lubricating viscosity range. For example, they may range in viscosities of from about 45 SSU at 100° to about 6000 SSU at 100° F., and preferably, from about 50 to about 250 SSU at 210° F. These oils may have viscosity indexes ranging to about 100 or higher. Viscosity indexes from about 70 to about 95 are preferred. The average moleculear weights of these oils may range from about 250 to about 800.

In instances where synthetic oils, or combinations thereof, with mineral oils are preferred, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones(polysiloxanes), alkyl-substituted diphenyl ethers typified by a butyl-substituted bis(p-phenoxy phenol)ether, phenoxy phenylethers. It is to be understood, however, that the compositions contemplated herein can also contain other materials. For example, detergents, dispersants, corrosion inhibitors, extreme pressure agents, viscosity index improvers, co-antioxidants, anti-wear agents and the like can be used, including metal phenates, metallic sulfonates, zinc phosphorodithioates, polymeric detergents and silicone defoamants. These materials do not detract from the value of the compositions of this invention, but rather they serve to impart their customary properties to the particular compositions in which they are incorporated. In general, the preformed adducts of the present invention may be employed in any amount which is effective for imparting one or more of fuel use reduction, anticorrosion and antiwear activity. In a more limited aspect, however, the adduct is effectively employed for these purposes in amounts from about 0.1% to about 10% by weight, and preferably from about 0.5 to about 5% of the total weight of the composition.

With respect to the greases of the invention, a wide variety of thickening agents can be used to prepare them. Included among the useful thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitric acid, myristic acid and hydrogenated fish oils.

Other thickening agents include salt and salt-soap complexes as calcium stearate-acetate (U.S. Pat. No. 2,197,263), barium stearate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions ae essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum slicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, preferably from 3 percent to 15, percent by weight of the total grease composition.

The liquid fuels contemplated include liquid hydrocarbon fuels such as fuel oils, diesel oils and gasolines and alcohol fuels such as methanol and ethanol or mixtures of these fuels. The effective amount of additive therein for fuel use reduction will range from about 5 pounds to about 1,000 pounds thereof per 1000 barrels of fuel, preferably from about 20 pounds to about 50 pounds per 1000 barrels.

The following Examples will illustrate the invention. It will be understood that they are illustrative only and are not meant to limit the scope of the invention.

EXAMPLE 1

Di-n-butyl 2,6-Di-tert-butylphenyl Borate

In a reaction system protected from moisture there was added to 2,6-di-tert-butylphenol (154.7 g), heated at 240°–260° C. while stirring, 141 g of tri-n-butyl borate in portions during about 4.5 hrs. A mixture of n-butanol with smaller amounts of unreacted tri-n-butyl borate and minor amounts of unreacted 2,6-di-tert-butylphenol was continuously distilled from the reaction mixture during the addition period. After addition was completed, the mixture was heated at 250° C. for one additional hour. Unreacted 2,6-di-tert-butylphenol was distilled from the mixture up to a pot temperature of 106° C. at a pressure of less than 0.05 mm of mercury, leaving the product, di-n-butyl-2,6 di-tert-butylphenyl borate, as a viscous amber oil (154 g).

EXAMPLE 2

Reaction of Di-n-butyl-2,6-Di-tert-butylphenyl Borate with 2,2'-Thiobis-(4-tert-octyl)phenol (1:1 molar ratio)

A mixture of di-n-butyl-2,6-di-tert-butylphenyl borate (72.4 g) prepared in Example 1 and 2,2'-thiobis-(4-tert-octylphenol (88.6 g) was heated at 240° to 242° C. during 1.25 hrs., during which n-butanol distilled from the reaction mixture. Any remaining volatile components were distilled to a pot temperature of 125° C. at less than 0.1 mm of mercury pressure. The reaction product was a dark amber tacky semisolid.

EXAMPLE 3

Reaction of Di-n-Butyl 2,6-Di-tert-butylphenyl Borate with 2,2'-Thio-bis-(4-tert-octyl)phenol (2:1 molar ratio)

By the method of Example 2, a mixture of di-n-butyl 2,6-di-tert-butylphenyl borate (72.4 g) prepared in Example 1 and 2,2'-thiobis-(4-tert-octyl)phenol (44.3 g) was heated at 240° C. for 2.5 hrs., during which n-butanol was distilled from the reaction mixture. The process was completed by stripping at a pot temperature of 115° C. at a pressure of less than 0.1 mm of mercury. The product was a brown solid.

EXAMPLE 4

Sequential Reaction of 2,6-Di-tert-butylphenol with Boric Anhydride and 4-tert-Butylcatechol (3:1:1 molar ratios)

2,6-Di-tert-butylphenol (206.3 g) was heated at 225°–238° C. and while stirring boric anhydride (26.5 g) was added in portions during about 2 hr. Stirring and heating were continued for 3 hrs. after the addition was completed. 4-tert-Butylcatechol (58.3 g) was then added in portions over a 2 hr. period, and heating at 225°–238° C. was continued for an additional 3 hr. period. Volatiles, including unreacted 2,6-di-tert-butylphenol, were removed by heating to a pot temperature of 125° C. under a pressure of less than 0.1 mm of mercury. The product removed was a very viscous dark amber oil.

EXAMPLE 5

Sequential Reaction of 2,6-Di-tert-Butylphenol with Boric Anhydride and 4-tert-Butylcatechol (Excess)

To an aliquot portion of the reaction product of Example 4 (53.6 g) there was added 4-tert-butylcatechol (41 g) and the mixture was heated at 225° C. for several hours during which more than 2 ml. of water was distilled from the reaction. The remaining reaction mixture was heated at a pot temperature of 125° C. under a reduced pressure of less than 0.21 mm of mercury to remove unreacted 4-tert-butylcatechol and any other volatiles. The product, mixed 2,6-di-tert-butylphenyl pyrocatechyl borate ester, was obtained as a hard amber solid (65.3 g).

EVALUATION OF COMPOUNDS

The products were evaluated for their oxidative stability in a 260 second solvent paraffinic neutral mineral oil. In most cases improvements in oxidative stability over the base oil were observed. In the test the sample lubricant is subjected to a stream of air which is bubbled through at the rate of 5 liters per hour at 325° F. for 40 hours. Present in the composition are samples of metals commonly used in engine construction, namely, iron, copper, aluminum and lead. See U.S. Pat. No. 3,682,980, incorporated herein by reference, for further details of the test. Improvement in viscosity index or neutralization number (or both) shows effective control. The results are shown in Table 1.

TABLE 1

| Composition Tested | Conc. Additive % Wt. | NN | KV, % | Pb Loss |
| --- | --- | --- | --- | --- |
| Oil | None | 17.8 | 202 | 171.3 |
|  |  | 17.0 | 334 | 66 |
| Example 1 | 1.0 | 5.7 | 88 | 0 |
|  | 0.5 | 6.9 | 104 | 0 |
| Example 2 | 1.0 | 1.2 | 17 | 0 |
|  | 0.5 | 4.1 | 43 | 0 |
| Example 3 | 1.0 | 3.2 | 19 | 0 |
|  | 0.5 | 4.7 | 18 | 0 |
| Example 4 | 1.0 | 0.5 | 5 | 0 |
|  | 0.5 | 0.5 | 4 | 0 |
| Example 5 | 1.0 | 6.4 | 5 | 0 |
|  | 0.5 | 5.2 | 5 | 0 |

I claim:

1. A lubricant composition comprising a major proportion of a a lubricating oil or grease therefrom and an antioxidant amount of a compound of the formula

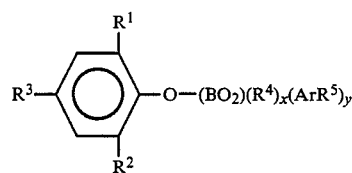

wherein
$R^1$ and $R^2$ are tertiary alkyl or aralkyl groups containing 4 to 8 carbon atoms;
$R^3$ is hydrogen or a hydrocarbyl group containing 1 to 18 carbon atoms, an alkoxy group containing 1 to 16 carbon atoms, an alkylaminomethylene group containing 4 to 16 carbon atoms or an alkylcarboxymethylene group containing 3 to 16 carbon atoms;
$R^4$ is hydrogen, a

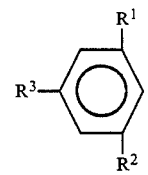

group, or a $C_1$ to $C_6$ alkyl group;

Ar is a $C_6$ to $C_{12}$ aromatic group;

$R^5$ is an alkoxy group containing 1 to 16 carbon atoms, an alkylaminomethylene group containing 4 to 16 carbon atoms or an alkylcarboxymethylene group containing 3 to 16 carbon atoms; a hydroxy group, a hydroxyarylthio group or a hydroxyarylamino group;

x is from 0 to 2; and y is 1 or 2.

2. The composition of claim 1 wherein the hydrocarbyl group is an alkyl, alkenyl, cycloalkyl, aryl, aralkyl or alkaryl group or a substituted member thereof.

3. The composition of claim 1 wherein the

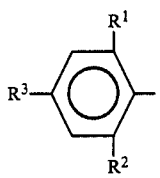

is derived from 2,6-di-t-butylphenol.

4. The composition of claim 1 wherein the

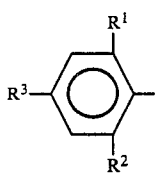

is derived from 2,6-di-t-butyl-4-butoxyphenol.

5. The composition of claim 1 wherein the

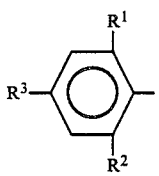

is derived from 2,6-di-t-butyl-4-carbobutoxyphenol.

6. The composition of claim 3, 4 or 5 wherein the

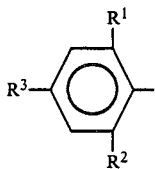

is derived from 3,6-di-t-butyl-4-hydroxybenzyl pivalate.

7. The composition of claim 1 wherein the $-ArR^5$ group is derived from t-butylcatechol.

8. The composition of claim 1 wherein the $-ArR^5$ group is derived from di-t-butylcatechol.

9. The composition of claim 1 wherein the $-ArR^5$ group is derived from n-hexylresorcinol.

10. The composition of claim 1 wherein the $-ArR^5$ group is derived from 2,4-di-t-butylphenol.

11. The composition of claim 1 wherein the $-ArR^5$ group is derived from t-butyl-p-cresol.

12. The composition of claim 1 wherein the $-ArR^5$ group is derived from amylhydroquinone.

13. The composition of claim 1 wherein the $-ArR^5$ group is derived from di-amylhydroquinone.

14. The composition of claim 1 wherein the $-ArR^5$ group is derived from dihexylnaphthol.

15. The composition of claim 1 wherein the $-ArR^5$ group is derived from 2,2'-thiobis-(4-t-amyl)phenol.

16. The composition of claim 1 wherein the $-ArR^5$ group is derived from 2,2'-thiobis-(4-t-octyl)phenol.

17. The composition of claim 1 wherein the $-ArR^5$ group is derived from carbobutoxyphenol.

18. The composition of claim 1 wherein the $-ArR^5$ group is derived from 4-anilinophenol.

19. The composition of claim 1 wherein the compound is

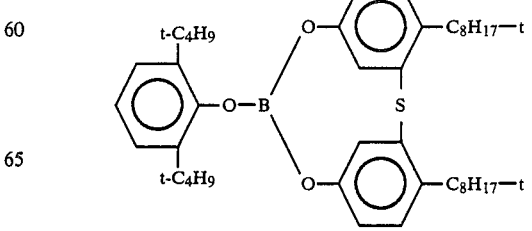

or

-continued

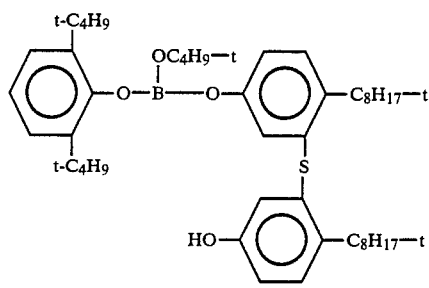

or mixtures thereof.

20. The composition of claim 1 wherein the compound is

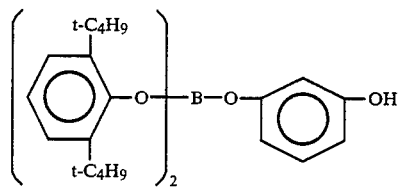

21. The composition of claim 1 wherein the lubricant is (1) a mineral lubricating oil, (2) a synthetic oil or mixture thereof, (3) mixtures of (1) and (2) and (4) a grease from any of (1), (2) and (3).

22. The composition of claim 21 wherein the lubricating oil is a mineral oil.

23. The composition of claim 21 wherein the lubricating oil is a synthetic oil or mixture thereof.

24. The composition of claim 21 wherein the lubricating oil is a mixture of mineral and synthetic oils.

25. The composition of claim 21 wherein the lubricant is a grease.

* * * * *

UNITED STATES PATENT AND TRADEMARK OFFICE
CERTIFICATE OF CORRECTION

PATENT NO. : 4,530,770

DATED : July 23, 1985

INVENTOR(S) : Milton Braid

It is certified that error appears in the above-identified patent and that said Letters Patent is hereby corrected as shown below:

Col. 6, line 53, "8" should read --18--.

Signed and Sealed this

Twenty-third Day of September 1986

[SEAL]

Attest:

DONALD J. QUIGG

Attesting Officer    Commissioner of Patents and Trademarks